(12) United States Patent
Hong et al.

(10) Patent No.: US 10,634,655 B2
(45) Date of Patent: Apr. 28, 2020

(54) METHOD FOR ANALYZING HEAVY METAL REMOVAL EFFICIENCY USING PHASE DIFFERENCE ANALYSIS AND APPARATUS USING THE SAME

(71) Applicant: ELECTRONICS AND TELECOMMUNICATIONS RESEARCH INSTITUTE, Daejeon (KR)

(72) Inventors: Hyo-Bong Hong, Daejeon (KR); Jae-Chan Jeong, Daejeon (KR); Seung-Min Choi, Daejeon (KR); Sung-Woong Shin, Daejeon (KR); Jae-Il Cho, Daejeon (KR); Nam-Shik Park, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 247 days.

(21) Appl. No.: 15/599,386

(22) Filed: May 18, 2017

(65) Prior Publication Data

US 2018/0011070 A1    Jan. 11, 2018

(30) Foreign Application Priority Data

Jul. 7, 2016    (KR) .................. 10-2016-0086319

(51) Int. Cl.
*G01N 33/18* (2006.01)
*G01N 27/02* (2006.01)
(Continued)

(52) U.S. Cl.
CPC ......... *G01N 33/1813* (2013.01); *C02F 1/281* (2013.01); *G01N 27/023* (2013.01);
(Continued)

(58) Field of Classification Search
CPC .... G01N 33/1813; G01N 27/023; C02F 1/281
See application file for complete search history.

(56) References Cited

U.S. PATENT DOCUMENTS

| 4,613,815 A | * | 9/1986 | Christel, Jr. ........... G01V 3/107 324/233 |
| 5,001,424 A | * | 3/1991 | Kellett ................... F16N 29/00 324/204 |

(Continued)

FOREIGN PATENT DOCUMENTS

| JP | 5212972 B2 | 3/2013 |
| KR | 20020080521 A | 10/2002 |

(Continued)

OTHER PUBLICATIONS

Tu et al., "Real-time measurement of Brownina relaxation of magnetic nanoparticles by a mixing-frequecny method", Applied Physics Letter, 2011, pp. 1-3, 98, 213702, AIP.

*Primary Examiner* — Krishnan S Menon
*Assistant Examiner* — Dwan A Gerido (57) ABSTRACT

Disclosed herein are a method for analyzing heavy metal removal efficiency using phase difference analysis and an apparatus using the method. The method for analyzing heavy metal removal efficiency using phase difference analysis includes applying a magnetic field to a magnetite onto which a heavy metal is adsorbed, based on a first solenoid coil and a second solenoid coil that have an identical winding direction, applying a high-frequency signal to the magnetite, based on a third solenoid coil having a winding direction that differs from that of the first solenoid coil and the second solenoid coil, detecting a high-frequency signal transformed by the magnetite, and calculating a phase difference between a previously detected default high-frequency signal and the transformed high-frequency signal, and analyzing an efficiency of heavy metal removal by the (Continued)

magnetite by measuring a concentration of the heavy metal based on the phase difference.

7 Claims, 8 Drawing Sheets

(51) Int. Cl.
| | |
|---|---|
| H01F 7/06 | (2006.01) |
| H01F 27/28 | (2006.01) |
| C02F 1/28 | (2006.01) |
| H01F 7/20 | (2006.01) |
| C02F 1/48 | (2006.01) |
| C02F 101/20 | (2006.01) |
| G01R 23/16 | (2006.01) |

(52) U.S. Cl.
CPC ............ *G01N 27/026* (2013.01); *H01F 7/06* (2013.01); *H01F 7/20* (2013.01); *H01F 27/2823* (2013.01); *C02F 1/488* (2013.01); *C02F 2101/20* (2013.01); *C02F 2209/003* (2013.01); *G01R 23/16* (2013.01)

(56) References Cited

U.S. PATENT DOCUMENTS

| | | |
|---|---|---|
| 5,910,729 A | 6/1999 | Yun |
| 6,666,972 B2 | 12/2003 | Lee |
| 8,115,478 B2 | 2/2012 | Fujii et al. |
| 2008/0073279 A1* | 3/2008 | Cort ........................ C02F 1/488 210/695 |
| 2015/0078644 A1 | 3/2015 | Park et al. |

FOREIGN PATENT DOCUMENTS

| | | |
|---|---|---|
| KR | 10-2005-0078461 A | 8/2005 |
| KR | 10-2006-0086481 A | 7/2006 |
| KR | 1020090025264 A | 3/2009 |
| KR | 10-2009-0060143 A | 6/2009 |
| KR | 10-1421077 B1 | 7/2014 |
| KR | 10-1506094 B1 | 3/2015 |
| KR | 1020150090356 A | 8/2015 |

\* cited by examiner

METHOD FOR ANALYZING HEAVY METAL REMOVAL EFFICIENCY USING PHASE DIFFERENCE ANALYSIS AND APPARATUS USING THE SAME

CROSS REFERENCE TO RELATED APPLICATION

This application claims the benefit of Korean Patent Application No. 10-2016-0086319, filed Jul. 7, 2016, which is hereby incorporated by reference in its entirety into this application.

BACKGROUND OF THE INVENTION

1. Technical Field

The present invention relates generally to technology for analyzing heavy metal removal efficiency in real time and, more particularly, to a method for analyzing heavy metal removal efficiency using phase difference analysis and an apparatus using the method, which use magnetite particles as a heavy metal adsorbent and analyze the phase difference of a signal transformed by the magnetite onto which a heavy metal is adsorbed, thus rapidly analyzing the efficiency of heavy metal removal.

2. Description of the Related Art

In modern society, one very important technology is to remove specific pollutants from a water system or to measure the efficiency of a system that removes pollutants. As a representative example thereof, one of the most important duties of water supply facilities is to separate and remove heavy metals, toxic organic materials, microorganisms, etc. from source water that flows from various sources by utilizing various types of adsorbents and chemical materials. For such separation and removal, various types of technologies and facilities have been developed in various industrial facilities in multiple fields, such as the environmental, chemical, and semiconductor fields.

However, the separation technology that has been most widely utilized at actual sites is to remove heavy metals and toxic organic materials contained in water using an adsorbent. To date, active carbon, zeolite, or alumina has been most widely used as the adsorbent. That is, heavy metals and toxic organic materials have been discarded by utilizing a method in which a material desired to be removed is adsorbed using the adsorbent, the adsorbed material is formed into sludge using a method such as precipitation or filtering, and the sludge is buried.

However, such a separation method using an adsorbent is disadvantageous in that materials used as the adsorbent are too expensive to be used once and be buried, and in that a method requiring a lot of time or cost, such as precipitation or filtering, must be used to recover (recycle) the used adsorbent. Further, it is difficult to actually check in real time the extent to which the adsorption of a heavy metal onto an expensive adsorbent has occurred, thus resulting in the waste of an expensive adsorbent without investing the amount of adsorbent that is actually needed at the site.

That is, the analysis technology that has been most widely used to date must directly extract a sample itself and use expensive analysis equipment that includes organic material analysis equipment such as for Inductively Coupled Plasma-Mass Spectrometry (ICP-MS), High Performance Liquid Chromatography (HPLC), or Gas Chromatography (GC), and metallic inorganic material analysis equipment such as for Inductively Coupled Plasma-Atomic Emission Spectrometry (ICP-AES) or Ion Chromatography (IC). Accordingly, this analysis technology is not suitable for site screening equipment for determining in real time whether to process materials.

Therefore, there is urgently required technology that is considered most important from the standpoint of system control and efficiency improvement, and that analyzes in real time the efficiency of removal of a heavy metal by an adsorbent.

In connection with this, Korean Patent Application Publication No. 10-2006-0086481 (Date of Publication: Jul. 31, 2006) discloses a technology related to "Density of Aerosol Sensing System Using Vibration Increaser Equipment and Capacitive Sensing Equipment."

SUMMARY OF THE INVENTION

Accordingly, the present invention has been made keeping in mind the above problems occurring in the prior art, and an object of the present invention is to provide a separation analysis system that is capable of analyzing adsorption efficiency in real time without using an expensive adsorbent.

Another object of the present invention is to provide a heavy metal removal system that is capable of recovering an adsorbent by using magnetite particles, which can be recycled in an environmentally friendly manner, as the adsorbent, without utilizing a method such as precipitation or filtering.

A further object of the present invention is to provide real-time screening technology that can be used at actual industrial sites.

Yet another object of the present invention is to provide a method that analyzes in real time the efficiency of heavy metal removal without utilizing expensive analysis equipment even if it is difficult to accurately know the kinds of material to be analyzed.

In accordance with an aspect of the present invention to accomplish the above objects, there is provided a method for analyzing heavy metal removal efficiency using phase difference analysis, including applying a magnetic field to a magnetite onto which a heavy metal is adsorbed, based on a first solenoid coil and a second solenoid coil that have an identical winding direction; applying a high-frequency signal to the magnetite, based on a third solenoid coil having a winding direction that differs from that of the first solenoid coil and the second solenoid coil; detecting a high-frequency signal transformed by the magnetite, and calculating a phase difference between a previously detected default high-frequency signal and the transformed high-frequency signal; and analyzing an efficiency of heavy metal removal by the magnetite by measuring a concentration of the heavy metal based on the phase difference.

Calculating the phase difference may be configured to convert the default high-frequency signal and the transformed high-frequency signal into respective frequency functions based on a Fast Fourier Transform (FFT), compare respective phases included in the frequency functions with each other, and then calculate the phase difference.

Analyzing the efficiency of heavy metal removal may be configured to measure the concentration of the heavy metal in proportion to the phase difference.

The first solenoid coil and the second solenoid coil may have forms in which enameled wires are wound around a first bobbin, having a sample inlet, in an identical winding direction to have a preset number of turns, and the third solenoid coil may have a form in which an enameled wire is wound around a second bobbin in a winding direction differing from that of the first solenoid coil and the second solenoid coil, wherein the second bobbin has a sample inlet smaller than that of the first bobbin and is located inside the first bobbin.

The default high-frequency signal may be a signal detected by applying the high-frequency signal, together with the magnetic field, to a magnetite onto which a heavy metal is not adsorbed.

Calculating the phase difference may be configured to extract a phase of the transformed high-frequency signal, obtained when a phase of the default high-frequency signal is set to '0', as a value of the phase difference.

Calculating the phase difference may be configured to detect the default high-frequency signal and the transformed high-frequency signal based on a Data Acquisition (DAQ) system that includes a function of at least one of an oscilloscope and a spectrum analyzer.

The method may further include separating the magnetite onto which the heavy metal is adsorbed from sewage water, to which the magnetite is added as an adsorbent, by utilizing an electromagnet.

In accordance with another aspect of the present invention to accomplish the above objects, there is provided an apparatus for analyzing heavy metal removal efficiency using phase difference analysis, including a magnetic field application unit for applying a magnetic field to a magnetite onto which a heavy metal is adsorbed, based on a first solenoid coil and a second solenoid coil that have an identical winding direction; a high-frequency signal application unit for applying a high-frequency signal to the magnetite, based on a third solenoid coil having a winding direction that differs from that of the first solenoid coil and the second solenoid coil; a phase difference calculation unit for detecting a high-frequency signal transformed by the magnetite, and calculating a phase difference between a previously detected default high-frequency signal and the transformed high-frequency signal; and a removal efficiency analysis unit for analyzing an efficiency of heavy metal removal by the magnetite by measuring a concentration of the heavy metal based on the phase difference.

The phase difference calculation unit may convert the default high-frequency signal and the transformed high-frequency signal into respective frequency functions based on a Fast Fourier Transform (FFT), compare respective phases included in the frequency functions with each other, and then calculate the phase difference.

The removal efficiency analysis unit may measure the concentration of the heavy metal in proportion to the phase difference.

The first solenoid coil and the second solenoid coil may have forms in which enameled wires are wound around a first bobbin, having a sample inlet, in an identical winding direction to have a preset number of turns, and the third solenoid coil may have a form in which an enameled wire is wound around a second bobbin in a winding direction differing from that of the first solenoid coil and the second solenoid coil, wherein the second bobbin has a sample inlet smaller than that of the first bobbin and is located inside the first bobbin.

The default high-frequency signal may be a signal detected by applying the high-frequency signal, together with the magnetic field, to a magnetite onto which a heavy metal is not adsorbed.

The phase difference calculation unit may extract a phase of the transformed high-frequency signal, obtained when a phase of the default high-frequency signal is set to '0', as a value of the phase difference.

The phase difference calculation unit may detect the default high-frequency signal and the transformed high-frequency signal based on a Data Acquisition (DAQ) system that includes a function of at least one of an oscilloscope and a spectrum analyzer.

The apparatus may further include a magnetite separation unit for separating the magnetite onto which the heavy metal is adsorbed from sewage water, to which the magnetite is added as an adsorbent, by utilizing an electromagnet.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Hereinafter, preferred embodiments of the present invention will be described in detail with reference to the attached drawings.

Figure 1:
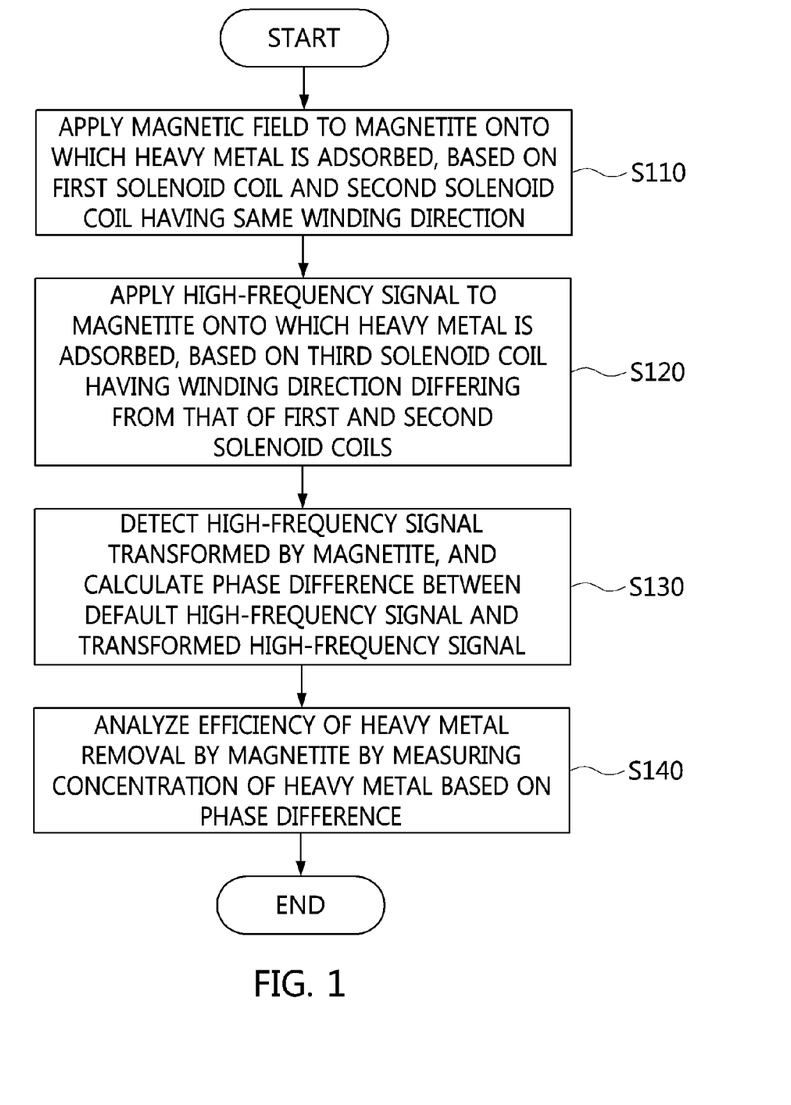
FIG. 1 is an operation flowchart illustrating a method for analyzing heavy metal removal efficiency using phase difference analysis according to an embodiment of the present invention.

FIG. 1 is an operation flowchart illustrating a method for analyzing heavy metal removal efficiency using phase difference analysis according to an embodiment of the present invention.

Referring to FIG. 1, the method for analyzing heavy metal removal efficiency using phase difference analysis according to the embodiment of the present invention applies a magnetic field to a magnetite onto which a heavy metal is adsorbed, based on a first solenoid coil and a second solenoid coil that have the same winding direction at step S110.

Here, magnetite particles having a micro-size or a nano-size may be used as an adsorbent. For example, about 1 g of magnetite particles having a size of 5.0 μm may be added to sewage water or polluted water containing a heavy metal or a toxic organic material and may be used as an adsorbent.

Here, Alternating Current (AC) may be individually applied to the first solenoid coil and to the second solenoid coil.

Here, in order to generate a magnetic field at a specific frequency, currents to be applied to the first solenoid coil and the second solenoid coil may be adjusted, and thus alternating currents having different strengths may be applied thereto. For example, an alternating current at a frequency ranging from 10 to 100 Hz may be applied to the first solenoid coil, and an alternating current at a frequency ranging from 10 to 100 kHz may be applied to the second solenoid coil.

Here, the first solenoid coil and the second solenoid coil may have forms in which enameled wires are respectively wound around a first bobbin having a sample inlet to have a preset number of turns in the same winding direction.

For example, the first solenoid coil may be formed in such a way that an enameled wire having a diameter of 0.1 mm is wound around the first bobbin, which has a length of about 10 cm and has a sample inlet with a length of about 15 mm, wherein the number of turns in the first solenoid coil is 500. Thereafter, the second solenoid coil may be formed in such a way that, after the enameled wire is insulated from the first solenoid coil, an enameled wire is wound around the first bobbin below the location at which the first solenoid coil is formed in the same winding direction as the first solenoid coil, wherein the number of turns in the second solenoid coil is 500.

Further, the method for analyzing heavy metal removal efficiency using phase difference analysis according to the embodiment of the present invention applies a high-frequency signal to the magnetite based on a third solenoid coil having a winding direction differing from that of the first solenoid coil and the second solenoid coil at step S120.

Here, the first bobbin and a second bobbin may each be formed in the shape of a cylindrical tube, and may be arranged such that the second bobbin, around which the third solenoid coil is wound, is fitted into the first bobbin, around which the first solenoid coil and the second solenoid coil are wound. Further, the magnetite onto which a heavy metal is adsorbed may enter the second bobbin through the sample inlet of the second bobbin, which is fitted into the first bobbin.

The magnetic field, which is generated based on the first solenoid coil and the second solenoid coil, together with the high-frequency signal, may be applied to the magnetite onto which a heavy metal is adsorbed.

Here, the third solenoid coil may have a form in which an enameled wire is wound around the second bobbin, which has a sample inlet smaller than that of the first bobbin and which is located in the first bobbin, in a winding direction differing from that of the first solenoid coil and the second solenoid coil. That is, the enameled wire is wound in the opposite direction from that of the first solenoid coil and the second solenoid coil, and thus the third solenoid coil may be formed.

Here, the high-frequency signal may be generated by amplifying the signal of the third solenoid coil.

That is, the magnetite located in the second bobbin may be excited with the high-frequency signal generated by the third solenoid coil, together with the magnetic field generated by the first solenoid coil and the second solenoid coil.

Then, the method for analyzing heavy metal removal efficiency using phase difference analysis according to the embodiment of the present invention detects a high-frequency signal transformed by the magnetite and calculates the phase difference between a previously detected default high-frequency signal and the transformed high-frequency signal at step S130.

Here, the default high-frequency signal may be a signal that is detected by applying a high-frequency signal, together with a magnetic field, to the magnetite onto which a heavy metal is not adsorbed.

Here, iron oxide particles, such as the magnetite, may perform a vibrational motion corresponding to any one of Brownian relaxation and Neel relaxation in a magnetic field region of an alternating current at a specific frequency. In this case, the vibrational motion may correspond to a vibration that occurs when magnetite particles are intended to be aligned along the direction of the magnetic field. The occurring vibrational motion results in a change in the phase of the high-frequency signal applied together with the magnetic field.

Due to the difference between the times at which respective vibrational motions occur in magnetite particles subjected to heavy metal adsorption and in magnetite particles not subjected to heavy metal adsorption, that is, relaxation times, a difference may occur between the degree of change in the phase of the default high-frequency signal and the degree of change in the phase of the transformed high-frequency signal.

Therefore, it may be possible to measure the amount of a heavy metal adsorbed onto the magnetite or the concentration of the heavy metal by calculating the difference between the phases of the two high-frequency signals.

Here, the phase difference between the default high-frequency signal and the transformed high-frequency signal may be calculated in such a way as to convert the default high-frequency signal and the transformed high-frequency signal into respective frequency functions based on a Fast Fourier Transform (FFT) and compare phases included in the respective frequency functions with each other.

Here, "FFT" may correspond to an efficient algorithm for performing a Discrete Fourier Transform (DFT) and an inverse DFT (IDFT) at high speed.

Further, "DFT" may correspond to a method of transforming signals on a time axis into signals in a frequency domain. Since all waves or waveforms may be represented by the sum of simple sine waves, the default high-frequency signal or the transformed high-frequency signal may also be represented by the resolved sum of sine waves at different frequencies.

Since a Fourier transform indicates amplitude and phase together based on a complex number, the phases of the default high-frequency signal and the transformed high-frequency signal may be easily checked based on the Fourier transform.

Therefore, respective phases of the default high-frequency signal and the transformed high-frequency signal may be checked, and thus the difference between the phases of the two signals may be calculated.

Here, the phase of the transformed high-frequency signal, obtained when the phase corresponding to the default high-frequency signal is set to '0', may be extracted as the value of the phase difference. For example, assuming that, when the phase of the default high-frequency signal is set to '0', the phase of the transformed high-frequency signal is 9, the phase difference may be calculated as 9°.

The default high-frequency signal and the transformed high-frequency signal may be detected based on a Data Acquisition (DAQ) system including the function of at least one of an oscilloscope and a spectrum analyzer.

Here, the DAQ system is intended to collect data about a physical phenomenon, and may be composed of a sensor, DAQ hardware, a signal conditioning part, and DAQ software. That is, in the present invention, data about the default high-frequency signal and the transformed high-frequency signal, which are physical waves, may be collected.

The oscilloscope is a device capable of visualizing variation in voltage in a specific band, and may be used to display periodically repeating electronic signals. That is, when the oscilloscope is used, a signal that varies over time may be detected in the form of a single periodically repeating voltage.

Here, the spectrum analyzer may be used to measure the energy distribution of modulated signals, such as Amplitude Modulated (AM) signals or Frequency Modulated (FM) signals, analyze the frequency of noise in the modulated signals, analyze harmonic and sub-harmonic components of the modulated signals, and measure the characteristics of the intermodulation product of the modulated signals or transmission lines.

Then, the method for analyzing heavy metal removal efficiency using phase difference analysis according to the embodiment of the present invention analyzes the efficiency of heavy metal removal by the magnetite by measuring the concentration of the heavy metal based on the phase difference at step S140.

Here, the concentration of the heavy metal may be measured in proportion to the phase difference. Therefore, it may be determined that, the greater the phase difference, the higher the concentration of the heavy metal that is detected by the magnetite. Therefore, the efficiency of heavy metal removal by the magnetite may be determined based on the detected heavy metal concentration. Even at actual sites, the amount of injection of the magnetite, as the adsorbent, may be determined.

Further, although not shown in FIG. 1, the method for analyzing heavy metal removal efficiency using phase difference analysis according to the embodiment of the present invention separates the magnetite (i.e. magnetite particles) onto which the heavy metal is adsorbed from the sewage water to which the magnetite is added as the adsorbent by utilizing an electromagnet.

For example, it may be assumed that magnetite particles are added as the adsorbent to sewage water containing an organic material such as arsenic chloride. Here, the sewage water and the adsorbent are desirably mixed, and the arsenic chloride is reacted with the magnetite particles so that the arsenic chloride is adsorbed onto the magnetite particles. Thereafter, the magnetite, which is a superparamagnetic material, may be separated from the sewage water using an electromagnet.

Here, instead of the electromagnet, a normal powerful magnet may be used. However, in the case of a normal magnet, it may be difficult to use the normal magnet in an actual process because the strength of the normal magnet must be controlled by adjusting the location of the normal magnet.

In this way, the present invention may reduce the time and cost by utilizing magnetite particles as the adsorbent and separating the magnetite particles using the electromagnet, compared to the case where the adsorbent is separated using a conventional method such as precipitation or filtering. Further, the magnetite that is used may be recycled, and thus an effect of cost reduction may be expected compared to the conventional scheme in which an expensive adsorbent must be used once and then buried.

As described above, through the use of the method for analyzing heavy metal removal efficiency using phase difference analysis, the present invention can provide a separation analysis system that is capable of analyzing adsorption efficiency in real time without using an expensive adsorbent.

Further, the present invention may recover an adsorbent by using magnetite particles that can be reused in an environmentally friendly manner as the adsorbent, without utilizing a conventional method such as precipitation or filtering.

Furthermore, the present invention may provide real-time screening technology that may be used at actual industrial sites, and may analyze in real time the efficiency of heavy metal removal without utilizing expensive analysis equipment even if it is difficult to accurately know the kinds of material to be analyzed.

Figure 2:
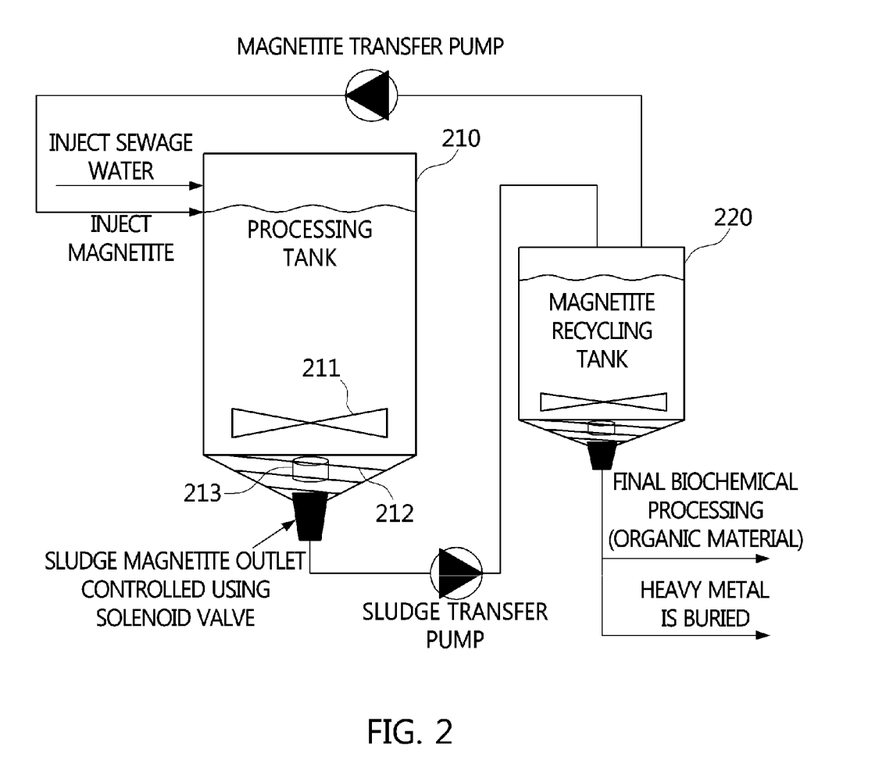
FIG. 2 is a diagram illustrating a system for removing a heavy metal and analyzing heavy metal removal efficiency according to an embodiment of the present invention.

FIG. 2 is a diagram illustrating a system for analyzing heavy metal removal efficiency according to an embodiment of the present invention.

Referring to FIG. 2, the system for analyzing heavy metal removal efficiency according to the embodiment of the present invention may include a processing tank 210 in which sewage water, containing a heavy metal, and a magnetite, that is, an adsorbent, are mixed, a mixer 211 for mixing the sewage water with the magnetite in the processing tank 210, a magnetite separation coil 212 for separating a magnetite (i.e. magnetite particles) onto which a heavy metal is adsorbed, and a phase detection device 213 for a high-frequency signal.

Below, a process for analyzing the efficiency of heavy metal removal will be sequentially described. First, sewage water containing a heavy metal or a toxic organic material may be injected into the processing tank 210.

Thereafter, a magnetite may be injected into the processing tank 210, and may be mixed with the sewage water through the mixer 211 so that the magnetite is reacted with the heavy metal and the toxic organic material.

Thereafter, when a material including a mixture of the sewage water and the magnetite is moved to a lower portion of the processing tank 210, only the magnetite onto which the heavy metal is adsorbed may be separated from the sewage water through the magnetite separation coil 212.

The separated magnetite may enter the phase detection device 213, and the phase of a high-frequency signal transformed by the magnetite may be detected.

Here, an apparatus for analyzing heavy metal removal efficiency according to the present invention may correspond to the magnetite separation coil 212 and the phase detection device 213, which are illustrated in FIG. 2.

Thereafter, the efficiency of heavy metal removal may be analyzed using the phase of the transformed high-frequency signal.

The magnetite formed into sludge may be moved to a magnetite recycling tank 220 through a sludge transfer pump, and may be separated from the heavy metal or toxic organic material in the magnetite recycling tank 220 and may then be recycled.

Figure 3:
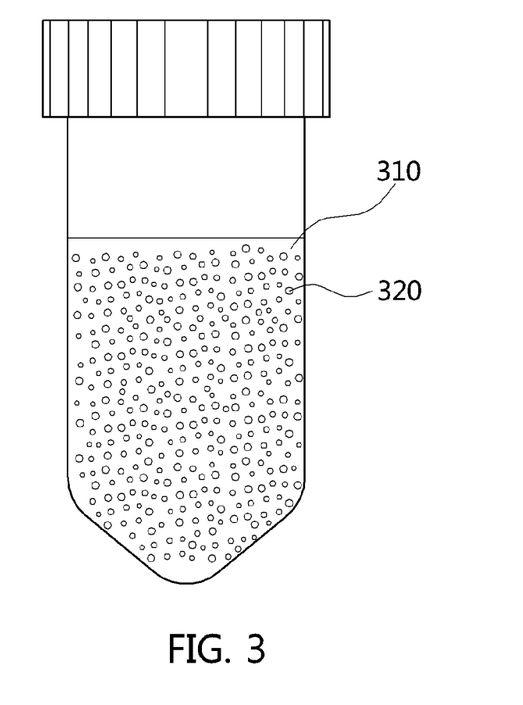
FIGS. 3 and 4 are diagrams illustrating a magnetite separation process according to an embodiment of the present invention.
Figure 4:
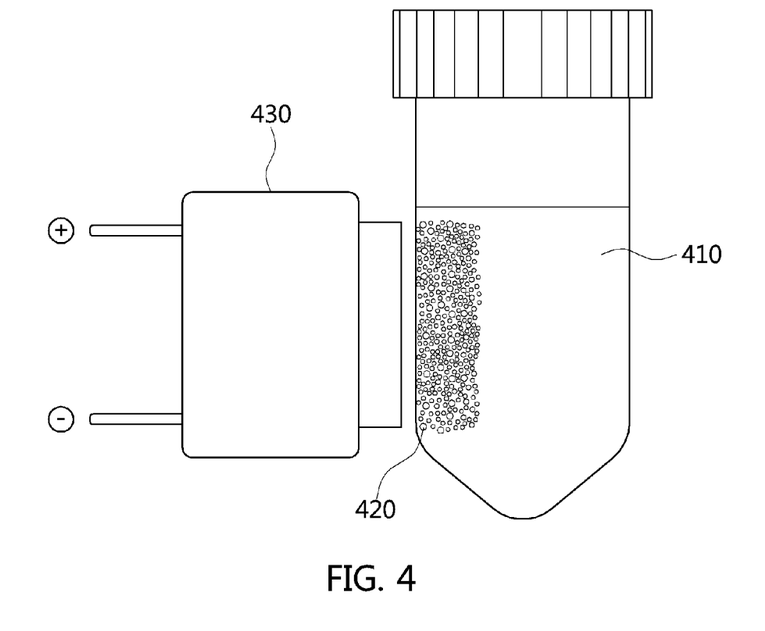

FIGS. 3 and 4 are diagrams illustrating a process for separating a magnetite according to an embodiment of the present invention.

Referring to FIGS. 3 and 4, it can be seen that a magnetite onto which a heavy metal is adsorbed is separated from sewage water 310 or 410, in which the heavy metal is mixed with the magnetite, by using an electromagnet 430 in accordance with an embodiment of the present invention.

Here, in an actual system for analyzing heavy metal removal efficiency, a magnetite separation coil functioning as the electromagnet 430 shown in FIG. 4 is provided in a processing tank into which sewage water is injected, thus enabling the magnetite onto which a heavy metal is adsorbed to be separated from the sewage water.

However, in FIG. 4, in order to show the process for actually separating a magnetite from the sewage water, separation using the electromagnet 430 is conducted. In this case, it may be possible to separate the magnetite using a normal powerful magnet, but it may be difficult to use the normal powerful magnet in the actual process because the strength of the normal powerful magnet must be controlled by adjusting the location of the normal powerful magnet relative to the sewage water 310 or 410.

Here, the adsorption and dispersion of the magnetite may be freely adjusted by utilizing the electromagnet 430, thus enabling process efficiency to be improved.

Referring to the sewage water 410 of FIG. 4, it can be seen that magnetite particles 420 onto which a heavy metal is adsorbed are separated to move towards the electromagnet 430, unlike the sewage water 310 of FIG. 3.

That is, before separation is conducted through the electromagnet 430, magnetite particles 320 are uniformly mixed with and distributed throughout the sewage water 310, as shown in FIG. 3. In contrast, in FIG. 4, the magnetite particles 420 may be separated to move towards one side of the sewage water due to the influence of the electromagnet 430.

Figure 5:
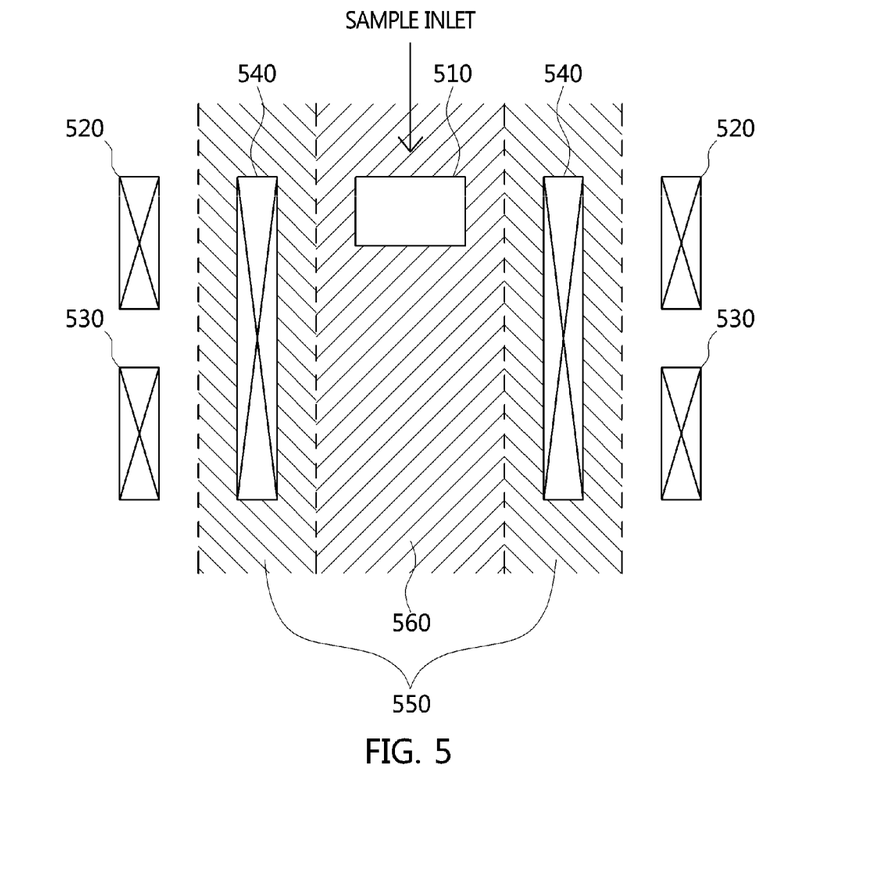
FIG. 5 is a diagram illustrating the arrangement of solenoid coils according to an embodiment of the present invention.

FIG. 5 is a diagram illustrating the arrangement of solenoid coils according to an embodiment of the present invention.

Referring to FIG. 5, solenoid coils according to the embodiment of the present invention may be arranged such that a first solenoid coil 520 and a second solenoid coil 530 are located in an outermost portion and such that a third solenoid coil 540 is located inside the first and second solenoid coils.

Here, the first solenoid coil 520 and the second solenoid coil 530 may be formed such that enameled wires are wound with the same number of turns in the same winding direction.

Here, the first solenoid coil 520 and the second solenoid coil 530 may be insulated from each other.

Each of the first solenoid coil 520 and the second solenoid coil 530 may be formed such that the enameled wire is wound around a first bobbin.

Further, the third solenoid coil 540 may be formed such that an enameled wire is wound in a winding direction differing from that of the first solenoid coil 520 and the second solenoid coil 530, and the number of turns in the third solenoid coil 540 is the sum of the numbers of turns in the first solenoid coil 520 and the second solenoid coil 530.

Here, the third solenoid coil 540 may be formed such that the enameled wire is wound around a second bobbin.

The first bobbin may have a sample inlet larger than that of the second bobbin, and the second bobbin may be arranged to be fitted into the first bobbin.

Therefore, the third solenoid coil 540 wound around the second bobbin may be located in an area 550 between the first bobbin and the second bobbin, and a sample 510 may enter the internal region 560 of the second bobbin through the sample inlet of the second bobbin.

Figure 6:
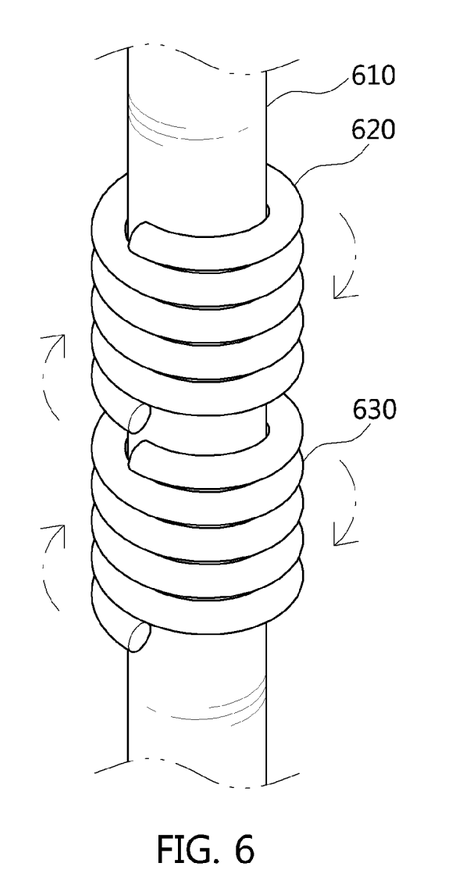
FIG. 6 is a diagram illustrating a first solenoid coil, a second solenoid coil, and a first bobbin according to an embodiment of the present invention.

FIG. 6 is a diagram illustrating a first solenoid coil, a second solenoid coil, and a first bobbin according to an embodiment of the present invention.

Referring to FIG. 6, a first solenoid coil 620 and a second solenoid coil 630 may be sequentially arranged around a first bobbin 610 according to an embodiment of the present invention.

Here, as shown in FIG. 6, the first solenoid coil 620 and the second solenoid coil 630 may be formed such that they have the same winding direction and such that enameled wires are wound with the same number of turns.

Although the first solenoid coil 620 or the second solenoid coil 630 shown in FIG. 6 is shown as having a smaller number of turns than that of an actual coil for the convenience of description, the first solenoid coil or the second solenoid coil may be formed such that the enameled wire is wound with a larger number of turns in actual devices.

Figure 7:
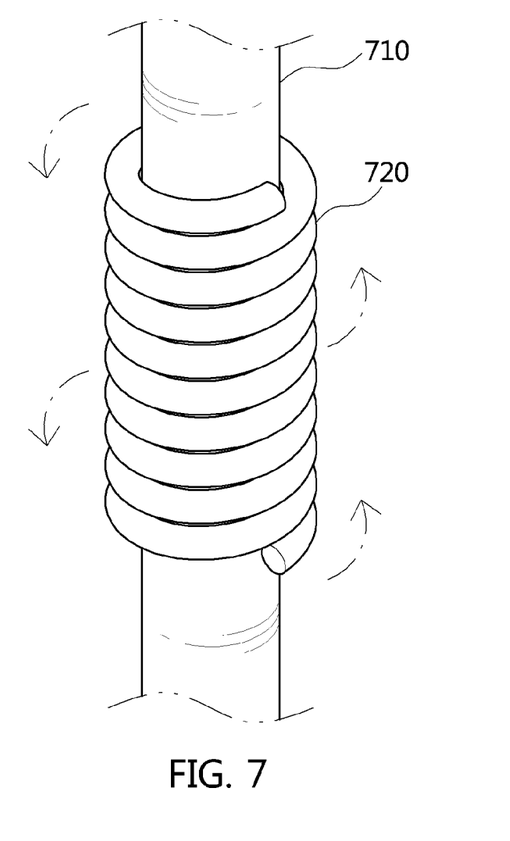
FIG. 7 is a diagram illustrating a third solenoid coil and a second bobbin according to an embodiment of the present invention.

FIG. 7 is a diagram illustrating a third solenoid coil and a second bobbin according to an embodiment of the present invention.

Referring to FIG. 7, a second bobbin 710 and a third solenoid coil 720 according to an embodiment of the present invention may be arranged.

Here, the third solenoid coil 720 may be formed such that an enameled wire is wound in the opposite direction from that of the first solenoid coil 620 and the second solenoid coil 630 shown in FIG. 6. Further, the third solenoid coil 720 may be formed such that the enameled wire is wound with a number of turns that is identical to the sum of the numbers of turns in the first solenoid coil 620 and the second solenoid coil 630 shown in FIG. 6.

Here, although the third solenoid coil 720 shown in FIG. 7 is shown as having a smaller number of turns than that of an actual coil for the convenience of description, the third solenoid coil may be formed such that the enameled wire is wound with a larger number of turns in actual devices.

Figure 8:
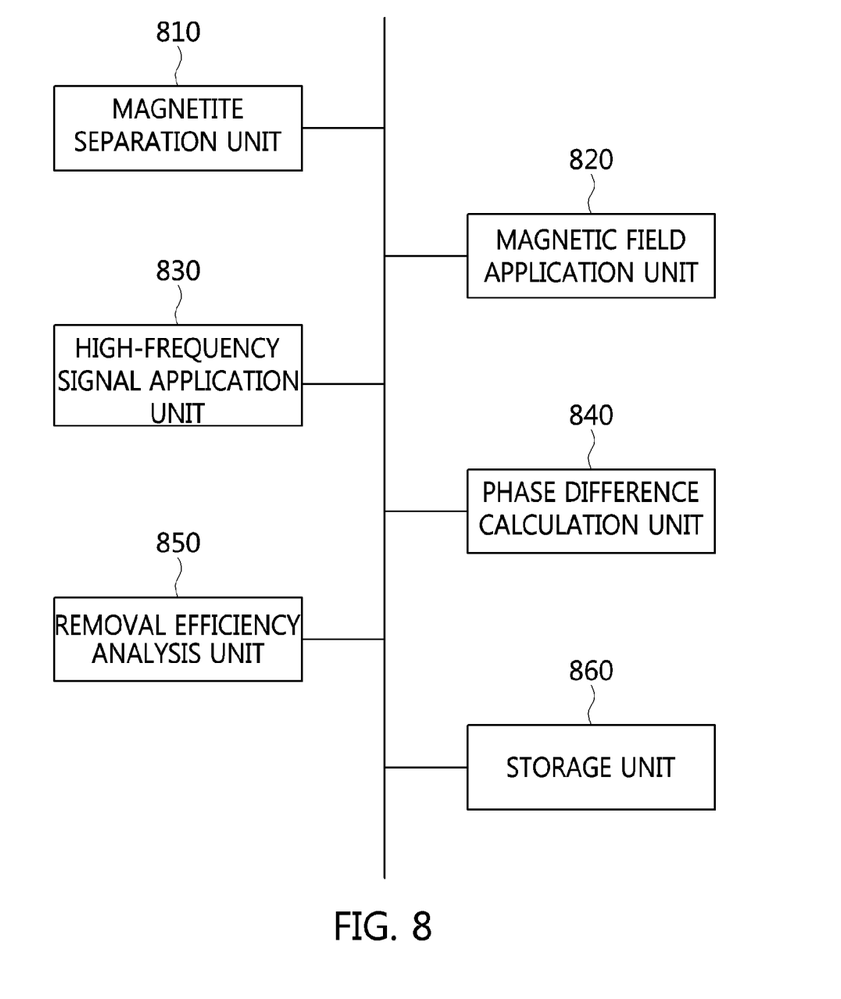
FIG. 8 is a block diagram illustrating an apparatus for analyzing heavy metal removal efficiency using phase difference analysis according to an embodiment of the present invention.

FIG. 8 is a block diagram illustrating an apparatus for analyzing heavy metal removal efficiency using phase difference analysis according to an embodiment of the present invention.

Referring to FIG. 8, the apparatus for analyzing heavy metal removal efficiency using phase difference analysis according to the embodiment of the present invention includes a magnetite separation unit 810, a magnetic field application unit 820, a high-frequency signal application unit 830, a phase difference calculation unit 840, a removal efficiency analysis unit 850, and a storage unit 860.

The magnetite separation unit 810 separates a magnetite onto which a heavy metal is adsorbed from sewage water, to which the magnetite is added as an adsorbent, by using an electromagnet.

For example, it may be assumed that magnetite particles are added as the adsorbent to sewage water containing an organic material such as arsenic chloride. Here, the sewage water and the adsorbent are desirably mixed, and the arsenic chloride is reacted with the magnetite particles so that the arsenic chloride is adsorbed onto the magnetite particles. Thereafter, the magnetite, which is a superparamagnetic material, may be separated from the sewage water using an electromagnet.

Here, instead of the electromagnet, a normal powerful magnet may be used. However, in the case of a normal magnet, it may be difficult to use the normal magnet in an actual process because the strength of the normal magnet must be controlled by adjusting the location of the normal magnet.

In this way, the present invention may reduce the time and cost by utilizing magnetite particles as the adsorbent and separating the magnetite particles using the electromagnet, compared to the case where the adsorbent is separated using a conventional method such as precipitation or filtering. Further, the magnetite that is used may be recycled, and thus an effect of cost reduction may be expected compared to the conventional scheme in which an expensive adsorbent must be used once and then buried.

The magnetic field application unit 820 applies a magnetic field to the magnetite onto which a heavy metal is adsorbed, based on a first solenoid coil and a second solenoid coil that have the same winding direction.

Here, magnetite particles having a micro-size or a nano-size may be used as an adsorbent. For example, about 1 g of magnetite particles having a size of 5.0 µm may be added to sewage water or polluted water containing a heavy metal or a toxic organic material and may be used as an adsorbent.

Here, Alternating Current (AC) may be individually applied to the first solenoid coil and to the second solenoid coil.

Here, in order to generate a magnetic field at a specific frequency, currents to be applied to the first solenoid coil and the second solenoid coil may be adjusted, and thus alternating currents having different strengths may be applied thereto. For example, an alternating current at a frequency ranging from 10 to 100 Hz may be applied to the first solenoid coil, and an alternating current at a frequency ranging from 10 to 100 kHz may be applied to the second solenoid coil.

Here, the first solenoid coil and the second solenoid coil may have forms in which enameled wires are respectively wound around a first bobbin having a sample inlet to have a preset number of turns in the same winding direction.

For example, the first solenoid coil may be formed in such a way that an enameled wire having a diameter of 0.1 mm is wound around the first bobbin, which has a length of about 10 cm and has a sample inlet with a length of about 15 mm, wherein the number of turns in the first solenoid coil is 500. Thereafter, the second solenoid coil may be formed in such a way that, after the enameled wire is insulated from the first solenoid coil, an enameled wire is wound around the first bobbin below the location at which the first solenoid coil is formed in the same winding direction as the first solenoid coil, wherein the number of turns in the second solenoid coil is 500.

The high-frequency signal application unit 830 applies a high-frequency signal to the magnetite based on a third solenoid coil having a winding direction differing from that of the first solenoid coil and the second solenoid coil.

Here, the first bobbin and a second bobbin may each be formed in the shape of a cylindrical tube, and may be arranged such that the second bobbin, around which the third solenoid coil is wound, is fitted into the first bobbin, around which the first solenoid coil and the second solenoid coil are wound. Further, the magnetite onto which a heavy metal is adsorbed may enter the second bobbin through the sample inlet of the second bobbin, which is fitted into the first bobbin.

The magnetic field, which is generated based on the first solenoid coil and the second solenoid coil, together with the high-frequency signal, may be applied to the magnetite onto which a heavy metal is adsorbed.

Here, the third solenoid coil may have a form in which an enameled wire is wound around the second bobbin, which has a sample inlet smaller than that of the first bobbin and which is located in the first bobbin, in a winding direction differing from that of the first solenoid coil and the second solenoid coil. That is, the enameled wire is wound in the opposite direction from that of the first solenoid coil and the second solenoid coil, and thus the third solenoid coil may be formed.

Here, the high-frequency signal may be generated by amplifying the signal of the third solenoid coil.

That is, the magnetite located in the second bobbin may be excited with the high-frequency signal generated by the third solenoid coil, together with the magnetic field generated by the first solenoid coil and the second solenoid coil.

The phase difference calculation unit 840 detects a high-frequency signal transformed by the magnetite and calculates the phase difference between a previously detected default high-frequency signal and the transformed high-frequency signal.

Here, the default high-frequency signal may be a signal that is detected by applying a high-frequency signal, together with a magnetic field, to the magnetite onto which a heavy metal is not adsorbed.

Here, iron oxide particles, such as the magnetite, may perform a vibrational motion corresponding to any one of Brownian relaxation and Neel relaxation in a magnetic field region of an alternating current at a specific frequency. In this case, the vibrational motion may correspond to a vibration that occurs when magnetite particles are intended to be aligned along the direction of the magnetic field. The occurring vibrational motion results in a change in the phase of the high-frequency signal applied together with the magnetic field.

Due to the difference between the times at which respective vibrational motions occur in magnetite particles subjected to heavy metal adsorption and in magnetite particles not subjected to heavy metal adsorption, that is, relaxation times, a difference may occur between the degree of change in the phase of the default high-frequency signal and the degree of change in the phase of the transformed high-frequency signal.

Therefore, it may be possible to measure the amount of a heavy metal adsorbed onto the magnetite or the concentration of the heavy metal by calculating the difference between the phases of the two high-frequency signals.

Here, the phase difference between the default high-frequency signal and the transformed high-frequency signal may be calculated in such a way as to convert the default high-frequency signal and the transformed high-frequency signal into respective frequency functions based on a Fast Fourier Transform (FFT) and compare phases included in the respective frequency functions with each other.

Here, "FFT" may correspond to an efficient algorithm for performing a Discrete Fourier Transform (DFT) and an inverse DFT (IDFT) at high speed.

Further, "DFT" may correspond to a method of transforming signals on a time axis into signals in a frequency domain. Since all waves or waveforms may be represented by the sum of simple sine waves, the default high-frequency signal or the transformed high-frequency signal may also be represented by the resolved sum of sine waves at different frequencies.

Since a Fourier transform indicates amplitude and phase together based on a complex number, the phases of the default high-frequency signal and the transformed high-frequency signal may be easily checked based on the Fourier transform.

Therefore, respective phases of the default high-frequency signal and the transformed high-frequency signal may be checked, and thus the difference between the phases of the two signals may be calculated.

Here, the phase of the transformed high-frequency signal, obtained when the phase corresponding to the default high-frequency signal is set to '0', may be extracted as the value of the phase difference. For example, assuming that, when the phase of the default high-frequency signal is set to '0', the phase of the transformed high-frequency signal is 9, the phase difference may be calculated as 9°.

The default high-frequency signal and the transformed high-frequency signal may be detected based on a Data Acquisition (DAQ) system including the function of at least one of an oscilloscope and a spectrum analyzer.

Here, the DAQ system is intended to collect data about a physical phenomenon, and may be composed of a sensor, DAQ hardware, a signal conditioning part, and DAQ software. That is, in the present invention, data about the default high-frequency signal and the transformed high-frequency signal, which are physical waves, may be collected.

The oscilloscope is a device capable of visualizing variation in voltage in a specific band, and may be used to display periodically repeating electronic signals. That is, when the oscilloscope is used, a signal that varies over time may be detected in the form of a single periodically repeating voltage.

Here, the spectrum analyzer may be used to measure the energy distribution of modulated signals, such as Amplitude Modulated (AM) signals or Frequency Modulated (FM) signals, analyze the frequency of noise in the modulated signals, analyze harmonic and sub-harmonic components of the modulated signals, and measure the characteristics of the intermodulation product of the modulated signals or transmission lines.

The removal efficiency analysis unit 850 analyzes the efficiency of heavy metal removal by the magnetite by measuring the concentration of the heavy metal based on the phase difference.

Here, the concentration of the heavy metal may be measured in proportion to the phase difference. Therefore, it may be determined that, the greater the phase difference, the higher the concentration of the heavy metal that is detected by the magnetite. Therefore, the efficiency of heavy metal removal by the magnetite may be determined based on the detected heavy metal concentration. Even at actual sites, the amount of injection of the magnetite, as the adsorbent, may be determined.

The storage unit 860 stores various types of information that occur during the process for analyzing heavy metal removal efficiency according to the embodiment of the present invention, as described above.

In accordance with an embodiment, the storage unit 860 may be implemented independently of the apparatus for analyzing heavy metal removal efficiency, and may then support a function for the analysis of heavy metal removal efficiency. Here, the storage unit 860 may function as separate large-capacity storage, and may include a control function for performing related operations.

Meanwhile, the apparatus for analyzing heavy metal removal efficiency may be equipped with memory and may store information therein. In an embodiment, the memory is a computer-readable medium. In an embodiment, the memory may be a volatile memory unit, and in another embodiment, the memory may be a nonvolatile memory unit. In an embodiment, a storage device may be a computer-readable medium. In various different embodiments, the storage device may include, for example, a hard disk device, an optical disk device or any other large-capacity storage device.

As described above, through the use of the apparatus for analyzing heavy metal removal efficiency using phase difference analysis, the present invention can provide a separation analysis system that is capable of analyzing adsorption efficiency in real time without using an expensive adsorbent.

Further, the present invention may recover an adsorbent by using magnetite particles that can be reused in an environmentally friendly manner as the adsorbent, without utilizing a conventional method such as precipitation or filtering.

Furthermore, the present invention may provide real-time screening technology that may be used at actual industrial sites, and may analyze in real time the efficiency of heavy metal removal without utilizing expensive analysis equipment even if it is difficult to accurately know the kinds of material to be analyzed.

As described above, in the method for analyzing heavy metal removal efficiency using phase difference analysis and the apparatus using the method according to the present invention, the configurations and schemes in the above-described embodiments are not limitedly applied, and some or all of the above embodiments can be selectively combined and configured so that various modifications are possible.

What is claimed is:

1. An apparatus for analyzing heavy metal removal efficiency using phase difference analysis, comprising:
   one or more processors; and
   a non-transitory computer-readable medium which has stored thereon computer-executable instructions to cause the one or more processors to perform:
   applying a magnetic field to a magnetite onto which a heavy metal is adsorbed, based on a first solenoid coil and a second solenoid coil that have an identical winding direction;
   applying a high-frequency signal to the magnetite, based on a third solenoid coil having a winding direction that differs from that of the first solenoid coil and the second solenoid coil;
   detecting a high-frequency signal transformed by the magnetite, and calculating a phase difference between a previously detected default high-frequency signal and the transformed high-frequency signal; and
   analyzing an efficiency of heavy metal removal by the magnetite by measuring a concentration of the heavy metal based on the phase difference,
   wherein the first solenoid coil and the second solenoid coil have forms in which enameled wires are wound around a first bobbin, having a sample inlet, in an identical winding direction to have a preset number of turns, and
   the third solenoid coil has a form in which an enameled wire is wound around a second bobbin in a winding direction that is different from that of the first solenoid coil and the second solenoid coil, wherein the second bobbin has a sample inlet smaller than that of the first bobbin and is located inside the first bobbin.

2. The apparatus of claim 1, wherein the one or more processors are caused to further perform converting the default high-frequency signal and the transformed high-frequency signal into respective frequency functions based on a Fast Fourier Transform (FFT), comparing respective phases included in the frequency functions with each other, and then calculating the phase difference.

3. The apparatus of claim 2, wherein the phase difference calculation unit extracts a phase of the transformed high-frequency signal, obtained when a phase of the default high-frequency signal is set to '0', as a value of the phase difference.

4. The apparatus of claim 1, wherein the one or more processors are caused to further perform measuring the concentration of the heavy metal in proportion to the phase difference.

5. The apparatus of claim 1, wherein the default high-frequency signal is a signal detected by applying the high-frequency signal, together with the magnetic field, to a magnetite onto which a heavy metal is not adsorbed.

6. The apparatus of claim 1, wherein the one or more processors are caused to further perform detecting the default high-frequency signal and the transformed high-frequency signal based on a Data Acquisition (DAQ) system that includes a function of at least one of an oscilloscope and a spectrum analyzer.

7. The apparatus of claim 1, wherein the one or more processors are caused to further perform separating the magnetite onto which the heavy metal is adsorbed from sewage water, to which the magnetite is added as an adsorbent, by utilizing an electromagnet.

* * * * *